(12) United States Patent
Vaughn et al.

(10) Patent No.: US 6,613,950 B1
(45) Date of Patent: Sep. 2, 2003

(54) STRIPPING HYDROCARBON IN AN OXYGENATE CONVERSION PROCESS

(75) Inventors: Stephen N. Vaughn, Kingwood, TX (US); Luc R. M. Martens, Meise (BE); Shun C. Fung, Bridgewater, NJ (US); David C. Skouby, Succasunna, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 09/587,766

(22) Filed: Jun. 6, 2000

(51) Int. Cl.$^7$ ................................................ C07C 1/00
(52) U.S. Cl. ..................... 585/639; 585/638; 585/640
(58) Field of Search ........................... 585/638, 639, 585/640

(56) References Cited

U.S. PATENT DOCUMENTS

| | | | |
|---|---|---|---|
| 2,906,695 A | 9/1959 | Boston .................... 208/127 |
| 3,258,455 A | 6/1966 | Natta et al. .............. 260/93.7 |
| 3,305,538 A | 2/1967 | Natta et al. .............. 260/93.7 |
| 3,364,190 A | 1/1968 | Emrick .................... 260/93.7 |
| 3,645,992 A | 2/1972 | Elston ..................... 260/80.78 |
| 3,647,682 A | 3/1972 | Rabo et al. ............... 208/120 |
| 4,071,573 A | * 1/1978 | Owen et al. ............. 260/668 R |
| 4,076,698 A | 2/1978 | Anderson et al. ......... 526/348.6 |
| 4,238,631 A | 12/1980 | Daviduk et al. ........... 585/469 |
| 4,243,691 A | 1/1981 | Mohlenkamp, Jr et al. . 426/649 |
| 4,302,565 A | 11/1981 | Goeke et al. ............. 526/88 |
| 4,310,440 A | 1/1982 | Wilson et al. ............ 252/435 |
| 4,328,384 A | * 5/1982 | Daviduk et al. ........... 585/469 |
| 4,419,221 A | 12/1983 | Castagnos, Jr. et al. .... 208/113 |
| 4,431,856 A | * 2/1984 | Daviduk et al. ........... 585/469 |
| 4,440,871 A | 4/1984 | Lok et al. ................ 502/214 |
| 4,499,327 A | 2/1985 | Kaiser .................... 585/640 |
| 4,567,029 A | 1/1986 | Wilson et al. ............ 423/306 |
| 4,613,721 A | 9/1986 | Kaiser .................... 585/643 |
| 4,659,685 A | 4/1987 | Coleman, III et al. ...... 502/113 |
| 4,677,242 A | 6/1987 | Kaiser .................... 585/638 |
| 4,677,243 A | 6/1987 | Kaiser .................... 585/638 |
| 4,752,651 A | 6/1988 | Kaiser .................... 585/640 |
| 4,861,743 A | 8/1989 | Flank et al. .............. 502/214 |
| 4,861,938 A | 8/1989 | Lewis et al. .............. 585/640 |
| 5,095,163 A | 3/1992 | Barger .................... 585/640 |
| 5,096,684 A | 3/1992 | Guth et al. ............... 423/306 |
| 5,126,308 A | 6/1992 | Barger et al. ............. 502/214 |
| 5,157,181 A | 10/1992 | Stine et al. .............. 585/329 |
| 5,191,141 A | 3/1993 | Barger et al. ............. 585/640 |
| 5,278,345 A | 1/1994 | Janssen et al. ............ 585/640 |
| 5,475,182 A | 12/1995 | Janssen .................... 585/640 |
| 5,714,662 A | 2/1998 | Vora et al. ............... 585/640 |
| 5,714,663 A | 2/1998 | Serrand et al. ............ 585/648 |
| 5,744,680 A | 4/1998 | Mulvaney, III et al. ..... 585/640 |
| 5,817,906 A | * 10/1998 | Marker et al. ............ 585/640 |
| 5,892,079 A | 4/1999 | Wilson, Jr. ............... 556/11 |
| 5,904,880 A | 5/1999 | Sun ....................... 252/373 |
| 5,912,393 A | 6/1999 | Barger et al. ............. 585/640 |
| 5,914,433 A | 6/1999 | Marker .................... 585/313 |
| 5,927,063 A | 7/1999 | Janda et al. .............. 60/39.02 |
| 5,932,512 A | 8/1999 | Sun ....................... 502/214 |
| 5,952,538 A | 9/1999 | Vaughn et al. ............ 585/640 |
| 5,962,762 A | * 10/1999 | Sun et al. ................ 585/640 |
| 5,972,203 A | 10/1999 | Smith et al. .............. 208/113 |
| 6,005,155 A | * 12/1999 | Sun ....................... 585/640 |
| 6,023,005 A | * 2/2000 | Lattner et al. ............ 585/639 |
| 6,040,264 A | 3/2000 | Sun et al. ................ 502/214 |
| 6,046,371 A | 4/2000 | Wu et al. ................. 585/638 |
| 6,051,745 A | 4/2000 | Wu et al. ................. 585/638 |
| 6,051,746 A | 4/2000 | Sun et al. ................ 585/639 |
| 6,057,261 A | 5/2000 | Sun ....................... 502/341 |
| 6,121,503 A | 9/2000 | Janssen et al. ............ 585/640 |
| 6,121,504 A | * 9/2000 | Kuechler et al. .......... 585/640 |
| 6,137,022 A | 10/2000 | Kuechler et al. .......... 585/638 |
| 6,166,282 A | * 12/2000 | Miller .................... 585/638 |
| 6,187,983 B1 | * 2/2001 | Sun ....................... 585/638 |
| 6,245,703 B1 | * 6/2001 | Kuechler et al. .......... 502/22 |

FOREIGN PATENT DOCUMENTS

| | | |
|---|---|---|
| AU | 199852747 | 8/1999 |
| DE | 3 524 890 | 7/1985 |
| EP | 060 103 | 9/1982 |
| EP | 096 996 | 12/1983 |
| EP | 882 692 | 12/1998 |
| WO | WO 97/36845 | 10/1997 |
| WO | WO 99/15482 | 4/1999 |
| WO | WO 00/32543 | 6/2000 |

OTHER PUBLICATIONS

"Riser Reactor", *Fluidization and Fluid–Particle Systems*, pp. 48–59, F.A. Zenz and D.F. Othmer, Reinhold Corp. NY 1960. —no month.

Louge, Michael, "Experimental Techniques" *Circulating Fluidized Beds*, Blackie Academic & Professional, pp. 336–337 (1997)—no month.

Meier et al., *Atlas of Zeolite Structure Types*, 4th ed., (1996).—no month.

Blackwell and Patton, *J. Phys. Chem.*, 92, pp. 3965–3974 (1988.)—no month.

"Free Fall Reactor," *Fluidization Engineering*, D. Kunii and O. Levenspiel, John Wiley & Sons, Inc., (1969).—no month.

"MTO—has its time come?" Nitrogen & Methanol, No. 246, Jul.–Aug. 2000.

Barger et al., "Converting Natural Gas to Ethylene and Propylene by the UOP/Hydro MTO Process," 12$^{th}$ International Zeolite Conference 1999 Materials Research Society p. 567–573.—no month.

(List continued on next page.)

Primary Examiner—Nadine G. Norton
(74) Attorney, Agent, or Firm—Paul T. LaVoie

(57) ABSTRACT

A process for method for the production of olefin product from an oxygenate-containing feedstock includes exposing a silicoaluminophosphate catalyst to an oxygenate-containing feedstock in a reaction zone under conditions effective to convert the oxygenate-containing feedstock to an olefin product, by stripping at least a portion of the exposed catalyst with a stripping gas; and returning at least a portion of the stripped catalyst directly to the reaction zone.

19 Claims, 2 Drawing Sheets

OTHER PUBLICATIONS

Chang, "Methanol Conversion to Light Olefins," Catal. Rev.—Sci. Eng., 26(3&4), 323–345 (1984)—no month.

Kaeding et al., "Production of Chemicals from Methanol," Journal of Catalysis 61, 155–164 (1980)—no month.

Liang et al., "Characteristics and Performance of SAPO–34 Catalyst for Methanol–to–Olefin Conversion," Applied Catalysis, 64 (1990) 31–40—no month.

Marchi et al., "Catalytic Conversion of Methanol to Light Alkenes on SAPO Molecular Sieves," Applied Catalysis, 71 (1991) 139–152—no month.

* cited by examiner

STRIPPING HYDROCARBON IN AN OXYGENATE CONVERSION PROCESS

FIELD OF THE INVENTION

This invention relates to a method of converting an oxygenate feedstock to an olefin product. In particular, this invention is to a method for converting an oxygenate feedstock to an olefin product by contacting a silicoaluminophosphate catalyst with a feedstock, followed by stripping a portion of the catalyst and returning the stripped catalyst to the reaction zone.

BACKGROUND OF THE INVENTION

Olefins, particularly light olefins, have been traditionally produced from petroleum feedstocks by either catalytic or steam cracking. Oxygenates, however, are becoming an alternative feedstock for making light olefins. Particularly promising oxygenate feedstocks are alcohols, such as methanol and ethanol, dimethyl ether, methyl ethyl ether, diethyl ether, dimethyl carbonate, and methyl formate. Many of these oxygenates can be produced from a variety of sources including synthesis gas derived from natural gas; petroleum liquids; carbonaceous materials, including coal; recycled plastics; municipal wastes; or any appropriate organic material. Because of the wide variety of sources, alcohol, alcohol derivatives, and other oxygenates have promise as an economical, non-petroleum source for light olefin production.

One way of producing olefins is by the catalytic conversion of methanol using a silicoaluminophosphate (SAPO) molecular sieve catalyst. For example, U.S. Pat. No. 4,499,327 to Kaiser, discloses making olefins from methanol using any of a variety of SAPO molecular sieve catalysts. The process can be carried out at a temperature between 300° C. and 500° C., a pressure between 0.1 atmosphere to 100 atmospheres, and a weight hourly space velocity (WHSV) of between 0.1 and 40 hr$^{-1}$.

However, during conversion of oxygenates to light olefins, by-products are also formed. Representative by-products include alkanes (methane, ethane, propane, and larger), $C_4^+$ olefins, aromatic compounds, and carbon oxides. Carbonaceous deposits on and within the catalyst materials (also referred to as "coke") are also formed in the process. As the amount of these carbonaceous deposits increases, the catalyst begins to lose activity and, consequently, less of the feedstock is converted to the desired light olefin products. At some point, the build up of these carbonaceous deposits causes the catalyst to reduce its capability to convert the oxygenates to light olefins. Once a catalyst becomes deactivated, it must be removed from the reaction vessel and replaced with activated catalyst. To reduce catalyst costs, activated catalyst is obtained by removing the carbonaceous deposits from the deactivated catalyst. This process is typically referred to as regeneration, and typically takes place in a vessel called a regenerator.

Catalyst regeneration is typically accomplished by periodically removing the deactivated catalyst from the reactor vessel, burning off the carbonaceous material in the regenerator to reactivate or regenerate the catalyst, and returning the regenerated catalyst to the reactor. Prior to entering the regenerator, any volatile organic components which may be adsorbed onto the catalyst or located within its microporous structure may be stripped off using a substantially inert stripping gas e.g., steam. The regenerated catalyst is then returned to the reactor.

Recently, it has been shown that catalyst selectivity to light olefins increases if the level of coke on the catalyst is controlled in some manner. One way of controlling the rate and manner in which the catalyst accumulates coke is taught by U.S. Pat. No. 6,023,055 to Lattner et al, and assigned to the assignee of the present application. Lattner et al. discloses a process whereby the oxygenate exposed catalyst exiting the reaction zone is separated into two portions. One portion is returned to the reaction zone, and the other portion settles into a stripping zone prior to entering the regenerator.

Methods are needed which will maintain a desired level of coking on the molecular sieve catalyst during the conversion of oxygenates to olefins. The desired level of coke is that which optimizes light olefin selectivity and/or decreases the rate of deactivation. It is, therefore, an object of the invention to control the amount and manner at which coke deposits on the catalyst.

SUMMARY OF THE INVENTION

The present invention controls the manner in which coke deposits on catalysts, particularly small-pore molecular sieve catalysts. In achieving this object and other objects of the invention, including a process for the production of olefin product from an oxygenate-containing feedstock, the invention comprises: exposing a molecular sieve catalyst to an oxygenate-containing feedstock in a reaction zone under conditions effective to convert the oxygenate-containing feedstock to an olefin product; stripping at least a portion of the exposed catalyst with a stripping gas; and returning at least a portion of the stripped catalyst to the reaction zone without regeneration. The intermittent removal of hydrocarbons adhered to the catalyst during the stripping process provides a degree of operational control so as to control the manner in which coke, is deposited on the catalyst. The result is an increase in product selectivity to light olefins and an increase in catalyst lifetime. Following the stripping process at least a portion of the stripped catalyst is returned to the reaction zone thereby repeating the process, which is preferably a continuous process. Optionally, a portion of the stripped catalyst may be directed to a regenerator prior to its return to the reaction zone. However, at least a portion of the stripped catalyst is not regenerated before returning to the reaction zone.

Hydrocarbons that may be adhered to the catalyst include, but are not limited to, oxygenates, aromatics, parafins, and olefins. Preferably, the stripped catalyst contains less than 10% of the hydrocarbons by weight, more preferably less than 5%, even more preferably less than 2%, and most preferably less than 1% of the hydrocarbons by weight. Substantially all of the hydrocarbons are removed from the stripped catalyst when less than 1% by weight of the hydrocarbons remain on the stripped catalyst exclusive of coke. Coke is defined as hydrocarbons that are not effectively stripped from the catalyst. Aromatics and substituted aromatics are examples of coke in this application.

Another feature of the invention is the ratio of the catalyst's exposure time in the reaction zone to the time the exposed catalyst is being stripped. Preferably, the ratio is from 1:1 to 20:1 and more preferably greater than 20:1. Such ratios intend to show that the catalyst is exposed to feedstock for relatively shorter periods of time prior to stripping relative to conventional methods.

The present invention controls the manner in which coke is deposited on the catalyst by stripping the coke precursor molecules away from the catalyst to a greater extent relative to a catalyst that was not intermittently stripped of hydrocarbons. Therefore, the catalytic activity of the catalyst unexpectedly is maintained at optimal levels for longer periods of time because the catalyst is not as readily deactivated. The process of the invention also increases the selectivity to light olefins. Moreover, since the overall coke forming process is exothermic, a reduction in the amount of coke produced reduces the amount of heat produced thereby reducing the heat removal requirements of the process equipment.

BRIEF DESCRIPTION OF THE DRAWINGS

The present invention will be better understood by reference to the Detailed Description of the Invention when taken together with the attached drawings, wherein.

DETAILED DESCRIPTION OF THE INVENTION

Figure 1:
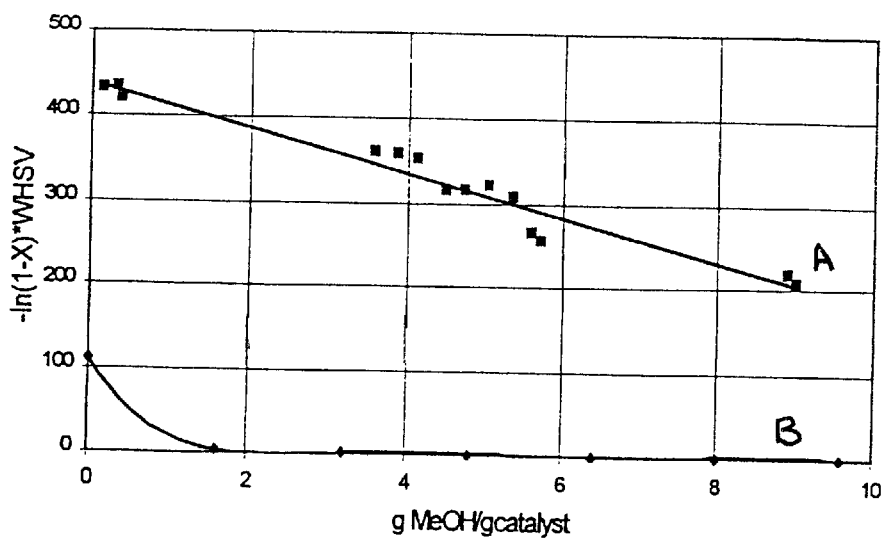
FIG. 1 illustrates the increase in catalytic activity using a morpholine templated SAPO-34 catalyst and the process of the present invention compared with a conventional continuous flow reactor.

The accumulation of coke deposits during conversion of oxygenates to light olefins gradually decreases the catalyst's activity and thus less feedstock is converted to the desired light olefins. Therefore it is desirable to control coke deposition on the catalyst during the conversion process to increase the catalyst's life and also to improve light olefin selectivity. The process of the invention provides operational flexibility in controlling the manner in which coke is deposited on the catalyst.

One embodiment of the present invention includes stripping at least a portion of the exposed catalyst with a stripping gas and returning at least a portion of the stripped catalyst directly to the reaction zone without regeneration. The term "at least a portion of" as used herein embodies acting upon some or all of the catalyst. Although the stripping step reduces the need for frequent regeneration, if the catalyst eventually requires regeneration, the process of the invention further includes regenerating a portion of the stripped catalyst before returning the catalyst to the reaction zone. At least a portion of the stripped catalyst is not regenerated before repeating the process of exposing the catalyst to the oxygenate-containing feedstock.

The catalyst that is used in the process of this invention is one that incorporates a silicoaluminophosphate (SAPO) molecular sieve. The molecular sieve comprises a three-dimensional microporous crystal framework structure of $[SiO_2]$, $[AlO_2]$ and $[PO_2]$ tetrahedral units. The way Si is incorporated into the structure can be determined by $^{29}Si$ MAS NMR. See Blackwell and Patton, *J. Phys. Chem.*, 92, 3965 (1988). The desired SAPO molecular sieves will exhibit one or more peaks in the $^{29}Si$ MAS NMR, with a chemical shift δ (Si) in the range of −88 to −96 ppm and with a combined peak area in that range of at least 20% of the total peak area of all peaks with a chemical shift δ (Si) in the range of −88 ppm to −115 ppm, where the δ (Si) chemical shifts refer to external tetramethylsilane (TMS).

The process of this invention is particularly effective for silicoaluminophosphate molecular sieves that deactivate quickly. These catalysts often have a relatively high $Si/Al_2$ ratio and/or a high selectivity to coke. In general, the lower the $Si/Al_2$ ratio, the lower the $C_1$–$C_4$ saturates selectivity, particularly propane selectivity. However, the process of the invention is particularly suitable for molecular sieves having a relatively high $Si/Al_2$ ratio, which can cost less to produce. A $Si/Al_2$ ratio of more than 0.25 to about 0.35 is desirable, with a $Si/Al_2$ ratio of greater than 0.35 to 0.45, being preferred, and a $Si/Al_2$ ratio of greater than 0.45 to about 0.65 being particularly preferred.

Silicoaluminophosphate molecular sieves are generally classified as being microporous materials having 8, 10, or 12 membered ring structures. These ring structures can have an average pore size ranging from about 3.5–15 angstroms. Preferred are the small pore SAPO molecular sieves having an average pore size of less than about 5 angstroms, preferably an average pore size ranging from about 3.5 to 5 angstroms, more preferably from 3.5 to 4.3 angstroms. These preferred pore sizes are typical of molecular sieves having 8 membered rings.

In general, silicoaluminophosphate molecular sieves comprise a molecular framework of corner-sharing $[SiO_2]$, $[AlO_2]$, and $[PO_2]$ tetrahedral units. This type of framework is effective in converting various oxygenates into olefin products.

The $[PO_2]$ tetrahedral units within the framework structure of the molecular sieve of this invention can be provided by a variety of compositions. Examples of these phosphorus-containing compositions include phosphoric acid, organic phosphates such as triethyl phosphate, and aluminophosphates. The phosphorous-containing compositions are mixed with reactive silicon and aluminum-containing compositions under the appropriate conditions to form the molecular sieve.

The $[AlO_2]$ tetrahedral units within the framework structure can be provided by a variety of compositions. Examples of these aluminum-containing compositions include aluminum alkoxides such as aluminum isopropoxide, aluminum phosphates, aluminum hydroxide, sodium aluminate, and pseudoboehmite. The aluminum-containing compositions are mixed with reactive silicon and phosphorus-containing compositions under the appropriate conditions to form the molecular sieve.

The $[SiO_2]$ tetrahedral units within the framework structure can be provided by a variety of compositions. Examples of these silicon-containing compositions include silica sols and silica alkoxides such as tetra ethyl orthosilicate. The silicon-containing compositions are mixed with reactive aluminum and phosphorus-containing compositions under the appropriate conditions to form the molecular sieve.

Substituted SAPOs can also be used in this invention. These compounds are generally known as MeAPSOs or metal-containing silicoaluminophosphates. The metal can be alkali metal ions (Group IA), alkaline earth metal ions (Group IIA), rare earth ions (Group IIIB, including the lanthanoid elements: lanthanum, cerium, praseodymium, neodymium, samarium, europium, gadolinium, terbium, dysprosium, holmium, erbium, thulium, ytterbium and lutetium; and scandium or yttrium) and the additional transition cations of Groups IVB, VB, VIB, VIIB, VIIIB, IB, and IIB.

Preferably, the Me represents atoms such as Zn, Mg, Mn, Co, Ni, Ga, Fe, Ti, Zr, Ge, Sn, and Cr. These atoms can be inserted into the tetrahedral framework through a $[MeO_2]$ tetrahedral unit. The $[MeO_2]$ tetrahedral unit carries a net electric charge depending on the valence state of the metal substituent. When the metal component has a valence state of +2, +3, +4, +5, or +6, the net electric charge is between −2 and +2. Incorporation of the metal component is typically accomplished adding the metal component during synthesis of the molecular sieve. However, post-synthesis ion exchange can also be used.

Suitable silicoaluminophosphate molecular sieves include SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO47, SAPO-56, the metal containing forms thereof, and mixtures thereof. Preferred are SAPO-17, SAPO-18, SAPO-34, SAPO44, and SAPO-47, particularly SAPO-18 and SAPO-34, including the metal containing forms thereof, and mixtures thereof. As used herein, the term mixture is synonymous with combination and is considered a composition of matter having two or more components in varying proportions, regardless of their physical state.

An aluminophosphate (ALPO) molecular sieve can also be used in the process of the present invention. Aluminophosphate molecular sieves are crystalline microporous oxides which can have an $AlPO_4$ framework. They can have additional elements within the framework, typically have uniform pore dimensions ranging from about 3 angstroms to about 10 angstroms, and are capable of making size selective separations of molecular species. More than two dozen structure types have been reported, including zeolite topological analogues. A more detailed description of the background and synthesis of aluminophosphates is found in U.S. Pat. No. 4,310,440, which is incorporated herein by reference in its entirety. Preferred ALPO structures are ALPO-5, ALPO-11, ALPO-18, ALPO-31, ALPO-34, ALPO-36, ALPO-37, and ALPO-46.

The ALPOs can also include a metal substituent in its framework. Preferably, the metal is selected from the group consisting of magnesium, manganese, zinc, cobalt, and mixtures thereof. These materials preferably exhibit adsorption, ion-exchange and/or catalytic properties similar to aluminosilicate, aluminophosphate and silica aluminophosphate molecular sieve compositions. Members of this class and their preparation are described in U.S. Pat. No. 4,567,029, incorporated herein by reference in its entirety.

The metal containing ALPOs have a three-dimensional microporous crystal framework structure of $MO_2$, $AlO_2$ and $PO_2$ tetrahedral units. These as manufactured structures (which contain template prior to calcination) can be represented by empirical chemical composition, on an anhydrous basis, as:

$$mR:(M_xAl_yP_z)O_2$$

wherein "R" represents at least one organic templating agent present in the intracrystalline pore system; "m" represents the moles of "R" present per mole of $(M_xAl_yP_z)O_2$ and has a value of from zero to 0.3, the maximum value in each case depending upon the molecular dimensions of the templating agent and the available void volume of the pore system of the particular metal aluminophosphate involved, "x", "y", and "z" represent the mole fractions of the metal "M", (i.e. magnesium, manganese, zinc and cobalt), aluminum and phosphorus, respectively, present as tetrahedral oxides.

The metal containing ALPOs are sometimes referred to by the acronym as MeAPO. Also in those cases where the metal "Me" in the composition is magnesium, the acronym MAPO is applied to the composition. Similarly ZAPO, MnAPO and CoAPO are applied to the compositions which contain zinc, manganese and cobalt respectively. To identify the various structural species which make up each of the subgeneric classes MAPO, ZAPO, CoAPO and MnAPO, each species is assigned a number and is identified, for example, as ZAPO-5, MAPO-11, CoAPO-34 and so forth.

The silicoaluminophosphate molecular sieves are synthesized by hydrothermal crystallization methods generally known in the art. See, for example, U.S. Pat. Nos. 4,440,871; 4,861,743; 5,096,684; and 5,126,308, the methods of making of which are fully incorporated herein by reference. A reaction mixture is formed by mixing together reactive silicon, aluminum and phosphorus components, along with at least one template. Generally the mixture is sealed and heated, preferably under autogenous pressure, to a temperature of at least 100° C., preferably from 100–250° C., until a crystalline product is formed. Formation of the crystalline product can take anywhere from around 2 hours to as much as 2 weeks. In some cases, stirring or seeding with crystalline material will facilitate the formation of the product.

Typically, the molecular sieve product will be formed in solution. It can be recovered by standard means, such as by centrifugation or filtration. The product can also be washed, recovered by the same means and dried.

As a result of the crystallization process, the recovered sieve contains within its pores at least a portion of the template used in making the initial reaction mixture. The crystalline structure essentially wraps around the template, and the template must be removed so that the molecular sieve can exhibit catalytic activity. Once the template is removed, the crystalline structure that remains has what is typically called an intracrystalline pore system.

In many cases, depending upon the nature of the final product formed, the template may be too large to be eluted from the intracrystalline pore system. In such a case, the template can be removed by a heat treatment process. For example, the template can be calcined, or essentially combusted, in the presence of an oxygen-containing gas, by contacting the template-containing sieve in the presence of the oxygen-containing gas and heating at temperatures from 200° C. to 900° C. In some cases, it may be desirable to heat in an environment having a low oxygen concentration. In these cases, however, the result will typically be a breakdown of the template into a smaller component, rather than by the combustion process. This type of process can be used for partial or complete removal of the template from the intracrystalline pore system. In other cases, with smaller templates, complete or partial removal from the sieve can be accomplished by conventional desorption processes such as those used in making standard zeolites.

The SAPO molecular sieve structure can be effectively controlled using combinations of templates. For example, in a particularly preferred embodiment, the SAPO molecular sieve is manufactured using a template combination of TEAOH and dipropylamine. This combination results in a particularly desirable SAPO structure for the conversion of oxygenates, particularly methanol and dimethyl ether, to light olefins such as ethylene and propylene. Other templates such as morpholine can also be used. In the morpholine case, generally two templates molecules can be contained within the SAPO core and thus, a higher acid site density can be achieved.

The silicoaluminophosphate molecular sieve is typically admixed (i.e., blended) with other materials. When blended, the resulting composition is typically referred to as a SAPO catalyst, with the catalyst comprising the SAPO molecular sieve.

Materials which can be blended with the molecular sieve can be various inert or catalytically active materials, or various binder materials. These materials include compositions such as kaolin and other clays, various forms of rare earth metals, metal oxides, other non-zeolite catalyst components, zeolite catalyst components, alumina or alumina sol, titania, zirconia, magnesia, thoria, beryllia, quartz, silica or silica or silica sol, and mixtures thereof These components are also effective in reducing, inter alia, overall catalyst cost, acting as a thermal sink to assist in heat shielding the catalyst during regeneration, densifying the catalyst and increasing catalyst strength. It is particularly desirable that the inert materials that are used in the catalyst to act as a thermal sink have a heat capacity of from about 0.05 to about 1 cal/g-° C., more preferably from about 0.1 to about 0.8 cal/g-° C., most preferably from about 0.1 to about 0.5 cal/g-° C.

Additional molecular sieve materials can be included as a part of the SAPO catalyst composition or they can be used as separate molecular sieve catalysts in admixture with the SAPO catalyst if desired. Structural types of small pore molecular sieves that are suitable for use in this invention include AEI, AFT, APC, ATN, ATT, ATV, AWW, BIK, CAS, CHA, CHI, DAC, DDR, EDL ERI, GOO, KFI, LEV, LOV, LTA, MON, PAU, PHI, RHO, ROG, THO, and substituted forms thereof Structural types of medium pore molecular sieves that are suitable for use in this invention include MFI, MEL, MTW, EUO, MTT, HEU, FER, AFO, AEL, TON, and substituted forms thereof. These small and medium pore molecular sieves are described in greater detail in the *Atlas of Zeolite Structural Types*, W. M. Meier and D. H. Olsen, Butterworth Heineman, 3rd ed., 1997, the detailed description of which is explicitly incorporated herein by reference. Preferred molecular sieves which can be combined with a silicoaluminophosphate catalyst include ZSM-5, ZSM-34, erionite, and chabazite.

The catalyst composition preferably comprises about 1% to about 99%, more preferably about 5% to about 90%, and most preferably about 10% to about 80%, by weight of molecular sieve. It is also preferred that the catalyst composition have a particle size of from about 20 $\mu$ to 3,000 $\mu$, more preferably about 30 $\mu$ to 200 $\mu$ is, most preferably about 50 $\mu$ to 150 $\mu$.

The catalyst can be subjected to a variety of treatments to achieve the desired physical and chemical characteristics. Such treatments include, but are not necessarily limited to hydrothermal treatment, calcination, acid treatment, base treatment, milling, ball milling, grinding, spray drying, and combinations thereof In this invention, a feed containing an oxygenate, and optionally a diluent or a hydrocarbon added separately or mixed with the oxygenate, is contacted with a catalyst containing a molecular sieve in a reaction zone or volume. The volume in which such contact takes place is herein termed the "reactor," which may be a part of a "reactor apparatus" or "reaction zone." Adjacent to the reactor is a stripper vessel, or alternatively a duct (located internal or external to the reactor) where stripping fluid is introduced.

Figure 3:
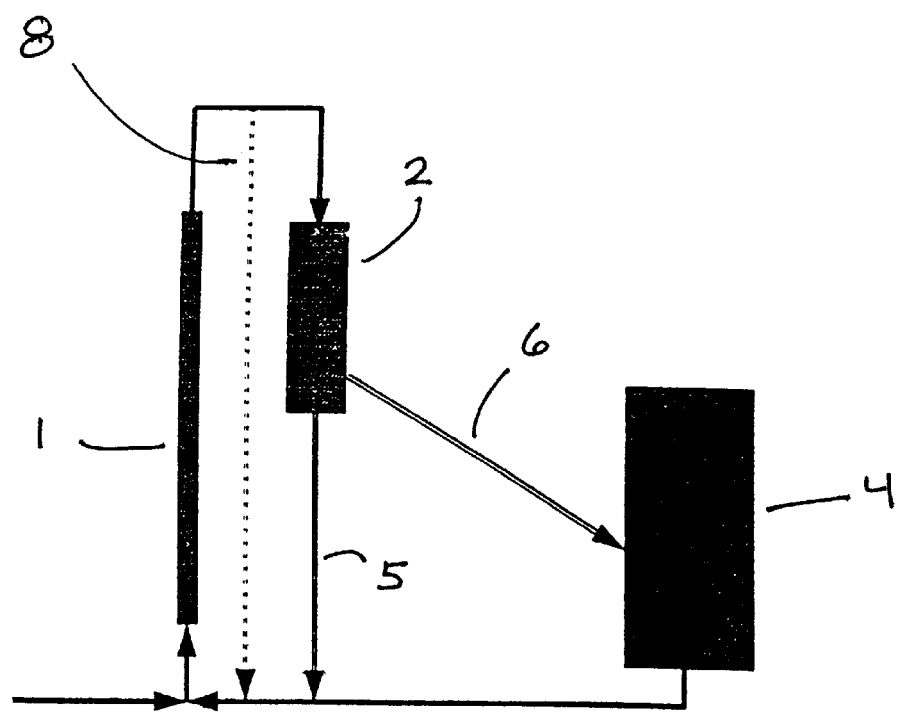
FIG. 3 is a schematic of an apparatus illustrating, in part, the catalyst's pathway from the stripper to the reactor.

Stripping fluid may comprise inert, non-condensible gases, such as $N_2$, Ar, $CO_2$, product gas, such as light and heavy olefins or fractions thereof, steam, or combinations thereof. As shown in FIG. 3, the stripper 2 or stripping vessel includes a pathway 5 from the stripper 2 to the reactor 1 that allows the catalyst to be returned directly to the reactor 1 without having to first pass through a regenerator 4. The regenerator comprises a volume wherein carbonaceous deposits (or coke) on the catalyst resulting from the oxygenate conversion reaction are removed by contacting the catalyst with regeneration medium. Preferably, the stripper is a separate unit apart from the regenerator to facilitate the return of the stripped catalyst to the reactor while bypassing the regenerator. Preferably, the stripper 2 also contains a pathway 6 from the stripper 2 to the regenerator 4 such that a portion of the catalyst can be passed to the regenerator 4 if desired. Preferably, two streams of catalyst are removed from the stripper; one stream is returned to the reaction zone and the other stream is sent to the regenerator.

In another embodiment of the invention, also shown in FIG. 3, at least a portion of exposed catalyst can be returned to the reaction zone by pathway 8, shown in phantom line, without having been stripped. The portion of the exposed catalyst that is stripped can then return to the reaction zone 1 along pathway 5 or proceed to the regenerator 4 along pathway 6.

The oxygenate feedstock of this invention comprises at least one organic compound which contains at least one oxygen atom, such as aliphatic alcohols, ethers, carbonyl compounds.(aldehydes, ketones, carboxylic acids, carbonates, esters and the like). When the oxygenate is an alcohol, the alcohol can include an aliphatic moiety having from 1 to 10 carbon atoms, more preferably from 1 to 4 carbon atoms. Representative alcohols include but are not necessarily limited to lower straight and branched chain aliphatic alcohols and their unsaturated counterparts. Examples of suitable oxygenate compounds include, but are not limited to: methanol; ethanol; n-propanol; isopropanol; $C_4$–$C_{20}$ alcohols; methyl ethyl ether; dimethyl ether; diethyl ether; di-isopropyl ether; formaldehyde; dimethyl carbonate; dimethyl ketone; acetic acid; and mixtures thereof. Preferred oxygenate compounds are methanol, dimethyl ether, or a mixture thereof.

The method of making the preferred olefin product in this invention can include the additional step of making these compositions from hydrocarbons such as oil, coal, tar sand, shale, biomass and natural gas. Methods for making the compositions are known in the art. These methods include fermentation to alcohol or ether, making synthesis gas, then converting the synthesis gas to alcohol or ether. Synthesis gas can be produced by known processes such as steam reforming, autothermal reforming and partial oxidization.

One or more inert diluents may be present in the feedstock, for example, in an amount of from 1 to 99 molar percent, based on the total number of moles of all feed and diluent components fed to the reaction zone (or catalyst). As defined herein, diluents are compositions which are essentially non-reactive across a molecular sieve catalyst, and primarily function to make the oxygenates in the feedstock less concentrated. Typical diluents include, but are not necessarily limited to helium, argon, nitrogen, carbon monoxide, carbon dioxide, water, essentially non-reactive paraffins (especially the alkanes such as methane, ethane, and propane), essentially non-reactive alkylenes, essentially non-reactive aromatic compounds, and mixtures thereof. The preferred diluents are water and nitrogen. Water can be injected in either liquid or vapor form.

Hydrocarbons can also be included as part of the feedstock, i.e., as co-feed. As defined herein, hydrocarbons included with the feedstock are hydrocarbon compositions which are converted to another chemical arrangement when contacted with molecular sieve catalyst. These hydrocarbons can include olefins, reactive paraffins, reactive alkylaromatics, reactive aromatics or mixtures thereof Preferred hydrocarbon co-feeds include, propylene, butylene, pentylene, $C_4^+$ hydrocarbon mixtures, $C_5^+$ hydrocarbon mixtures, and mixtures thereof. More preferred as co-feeds are a $C_4^+$ hydrocarbon mixtures, with the most preferred being $C_4^+$ hydrocarbon mixtures which are obtained from separation and recycle of reactor product.

Catalyst that has been contacted with feed in a reactor is defined herein as "feedstock exposed." Feedstock exposed catalyst will provide oxygenate conversion reaction products having substantially lower propane and coke content than a catalyst which is fresh and regenerated. A catalyst will typically provide lower amounts of propane as it is exposed to more feed, either through increasing time at a given feed rate or increasing feed rate over a given time.

In any process with continuous regeneration, at any given instant in time, some of the catalyst in the reactor will be fresh, some regenerated, and some coked or partially coked. Therefore, various portions of the catalyst in the reactor will have been feedstock exposed for different periods of time. Since the rate at which feed flows to the reactor can vary, the amount of feed to which various portions of the catalyst can also vary. To account for this variation, the "average catalyst feedstock exposure index (ACFE index)" is used to quantitatively define the extent to which the entire catalyst in the reactor has been feedstock exposed.

As used herein, ACFE index is the total weight of feed divided by the total weight of molecular sieve (i.e., excluding binder, inerts, etc., of the catalyst composition) sent to the reactor. The measurement should be made over an equivalent time interval, and the time interval should be long enough to smooth out fluctuations in catalyst or feedstock rates according to the reactor and regeneration process step selected to allow the system to be viewed as essentially continuous. In the case of reactor systems with periodic regenerations, this can typically range from hours up to days or longer. In the case of reactor systems with substantially constant regeneration, typically, minutes or hours may be sufficient.

Flow rate of catalyst can be measured in a variety of ways. In the design of the equipment used to carry the catalyst between the reactor and regenerator, the catalyst flow rate can be determined given the coke production rate in the reactor, the average coke level on catalyst leaving the reactor, and the average coke level on catalyst leaving the regenerator. In an operating unit with continuous catalyst flow, a variety of measurement techniques can be used. Many such techniques are described, for example, by Michel Louge, "Experimental Techniques," *Circulating Fluidized Beds*, Grace, Avidan, & Knowlton, eds., Blackie, 1997 (336–337), the descriptions of which are expressly incorporated herein by reference.

For the purpose of this invention, only the molecular sieve contained in the catalyst that is sent to the reactor is used in the determination of ACFE index. The catalyst sent to the reactor, however, can be either fresh or regenerated or a combination of both. Molecular sieve which may be recirculated to and from the reactor within the reactor apparatus (i.e., via ducts, pipes or annular regions), and which has not been regenerated or does not contain fresh catalyst, is not to be used in the determination of ACFE index.

In a preferred embodiment of this invention, a feed containing an oxygenate, and optionally a hydrocarbon, either separately or mixed with the oxygenate, is contacted with a catalyst containing a SAPO molecular sieve at process conditions effective to produce olefins in a reactor where the catalyst has an ACFE index of at least about 1.0, preferably at least 1.5. An ACFE index in the range of about 1.0 to 20 is effective, with a range of about 1.5–15 being desirable. A range of about 2–12 is particularly preferred. The invention substantially reduces the yield of coke, propane and other low value saturated by-products from an oxygenate conversion process compared to conventional processes.

The conversion of oxygenates to produce light olefins may be carried out in a variety of catalytic reactors. Reactor types include fixed bed reactors, fluid bed reactors, and concurrent riser reactors as described in "Free Fall Reactor," *Fluidization Engineering*, D. Kunii and O. Levenspiel, Robert E. Krieger Publishing Co. NY, 1977, expressly incorporated herein by reference. Additionally, countercurrent free fall reactors may be used in the conversion process as described in U.S. Pat. No. 4,068,136 and "Riser Reactor", *Fluidization and Fluid-Particle Systems*, pages 48–59, F. A. Zenz and D. F. Othmo, Reinhold Publishing Corp., NY 1960, the detailed descriptions of which are also expressly incorporated herein by reference.

Desirably, in an oxygenate to olefin conversion reaction conducted in the hydrocarbon conversion apparatus of the present invention employs a gas superficial velocity in the reactor of greater than 1 meter per second (m/s). As used herein and in the claims, the term, "gas superficial velocity," is defined as the volumetric flow rate of vaporized feedstock, and any diluent, divided by the reactor cross-sectional area. Because the oxygenate is converted to a product including a light olefin while flowing through the reactor, the gas superficial velocity may vary at different locations within the reactor depending on the total number of moles of gas present and the cross section of a particular location in the reactor, temperature, pressure, and other relevant reaction parameters. The gas superficial velocity, including any diluents present in the feedstock, is maintained at a rate greater than 1 meter per second (m/s) at any point in the reactor. Desirably, the gas superficial velocity is greater than about 2 m/s. More desirably, the gas superficial velocity is greater than about 2.5 m/s. Even more desirably, the gas superficial velocity is greater than about 4 m/s. Most desirably, the gas superficial velocity is greater than about 8 m/s.

Maintaining the gas superficial velocity at these rates increases the approach to plug flow behavior of the gases flowing in the reactor. As the gas superficial velocity increases above 1 m/s, a reduction in axial diffusion or back mixing of the gases results from a reduction in internal recirculation of solids, which carry gas with them. (Ideal plug flow behavior occurs when elements of the homogeneous fluid reactant move through a reactor as plugs moving parallel to the reactor axis). Minimizing the back mixing of the gases in the reactor increases the selectivity to the desired light olefins in the oxygenate conversion reaction.

When the gas superficial velocity approaches 1 m/s or higher, a substantial portion of the catalyst in the reactor may be entrained with the gas exiting the reactor. At least a portion of the catalyst exiting the reactor is recirculated to recontact the feed through the catalyst return.

A silicoaluminophosphate catalyst is exposed to an oxygenate-containing feedstock for from 1–20 seconds in a reactor under conditions effective to convert the oxygenate-containing feedstock to an olefin product. Preferably the catalyst is exposed to the feedstock for about 5–15 seconds, and more preferably about 7–12 seconds. This transit time may be adjusted by design of the superficial gas velocity and length of the reactor.

For the process of the invention, any standard reactor system that is capable of providing the means necessary to perform the process of the invention can be used. Such reactors include fixed bed, fluid bed or moving bed systems. Preferred reactors are co-current riser reactors, and short contact time, countercurrent free-fall reactors in which an oxygenate feedstock can be contacted with a molecular sieve catalyst at a WHSV of at least about 10 $hr^{-1}$, preferably in the range of from about 20 $hr^{-1}$ to 500 $hr^{-1}$, and most preferably in the range of from about 20 hr$^{-1}$ to 200 hr$^{-1}$. WHSV is defined herein as the weight of oxygenate, and hydrocarbon which may optionally be in the feed, per hour per weight of the molecular sieve content of the catalyst. Because the catalyst or the feedstock may contain other materials which act as inerts or diluents, the WHSV is calculated on the weight basis of the oxygenate feed, and any hydrocarbon which may be present, and the molecular sieve contained in the catalyst.

A non-limiting example of an apparatus useful to achieve the process of the invention is shown schematically in FIG. 3. In this embodiment, catalyst is picked up pneumatically by vaporized feed and optionally, lift steam, which flows upward through a riser or fast fluidized bed reaction zone. A combination of gas velocity and catalyst flow rate will determine the WHSV, described above, of the reactor. Transit time of the catalyst through the length of the reactor, and thus the exposure time to the feed, should be in range of 1–20 seconds and may be adjusted by design of the superficial gas velocity and length of the reactor.

Preferably, the oxygenate feed is contacted with the catalyst when the oxygenate is in a vapor phase. Alternatively, the process may be carried out in a liquid or a mixed vapor/liquid phase. When the process is carried out in a liquid phase or a mixed vapor/liquid phase, different conversions and selectivities of feed-to-product may result depending upon the catalyst and reaction conditions.

The process can generally be carried out at a wide range of temperatures. An effective operating temperature range can be from about 200° C. to 700° C., preferably from about 300° C. to 600° C., more preferably from about 350° C. to 550° C. At the lower end of the temperature range, the formation of the desired olefin products may become markedly slow. At the upper end of the temperature range, the process may not form an optimum amount of product.

It is desirable to operate at a temperature of at least 300° C. and a Temperature Corrected Normalized Methane Sensitivity (TCNMS) of less than about 0.016. It is particularly preferred that the reaction conditions for making olefin from oxygenate comprise a WHSV of at least about 20 hr$^{-1}$ producing olefins and a TCNMS of less than about 0.016.

As used herein, TCNMS is defined as the Normalized Methane Selectivity (NMS) when the temperature is less than 400° C. The NMS is defined as the methane product yield divided by the ethylene product yield wherein each yield is measured on, or is converted to, a weight % basis. When the temperature is 400° C. or greater, the TCNMS is defined by the following equation, in which T is the average temperature within the reactor in ° C.:

$$TCNMS = \frac{NMS}{1 + (((T - 400)/400) \times 14.84)}$$

The pressure also may vary over a wide range, including autogenous pressures. Effective pressures may be in, but are not necessarily limited to, oxygenate partial pressures at least 1 psia, preferably at least 5 psia. The process is particularly effective at higher oxygenate partial pressures, such as an oxygenate partial pressure of greater than 20 psia. Preferably, the oxygenate partial pressure is at least about 25 psia, more preferably at least about 30 psia. For practical design purposes it is desirable to operate at a methanol partial pressure of not greater than about 500 psia, preferably not greater than about 400 psia, most preferably not greater than about 300 psia.

With reference to FIG. 3, after discharging the solids from the product gas stream, the partially spent catalyst is then directed to either a stripper vessel 2 or alternatively, a duct located either internal or external to the reaction zone vessel 1, where stripping fluid is introduced. The stripping process removes the volatile organic components which may be adsorbed onto the catalyst or located within its microporous structure prior to returning to the reaction zone 1 or entering the regenerator 4. This can be accomplished by passing a stripping gas over the catalyst in a stripper or stripping chamber, which can be located in a separate vessel.

The stripping gas comprises (a) any substantially inert, non-condensable medium that is commonly used; (b) product gas or fractions thereof comprising ethylene, propylene and heavier olefins; (c) steam; or (d) combinations of a–c above. Preferred stripping gases comprise, for example, steam, nitrogen, helium, argon, methane, $CO_2$, CO, flue gas, and hydrogen, or combinations thereof, and more preferably a combination of inert gas and steam. Most preferably, the stripping gas comprises steam.

One feature of the invention is the extent of the stripping that is performed in the process of the invention, which is greater than that normally considered necessary to remove hydrocarbons, prior to transferring the catalyst to the reaction zone or to the regenerator. The most common stripping gas is steam. In the present invention, the stripping rate used is dependent upon the volatility of the products to be stripped off the catalyst prior to regeneration as well as such operational considerations as ensuring adequate contained carbon retained on the catalyst to control operating temperatures in the reactor and regenerater steps. Additionally, economic considerations such as energy efficiency, heating and cooling the stripper fluid and vessel size tend to limit the upper limit of how much stripper fluid is used. A stripping rate of 1–10 lb, preferably a rate of 1–4 lb, steam per hour per 1000 lb of catalyst per hour is typically used.

To increase the extent a catalyst is stripped a combination of increased residense time, i.e., larger stripping vessel or transfer line, and/or a greater flow rate of stripping fluid relative to the amount of catalyst in the stripping vessel or line, can be used. Also, the effectiveness of the stripping fluid must be considered.

In order to compare stripping rates of fluids other than steam, an Equivalent Steam Stripping Rate (ESSR) is defined for the purposes of the instant invention as:

$$ESSR = \frac{\text{volumetric flow rate of stripping fluid (at STP)}}{\text{volumetric flow rate of catalyst}}$$

STP is Standard Temperature and Pressure (273° C. and 101 kPa)

In the special case of a non-continuous catalyst feed, i.e., batch stripping, a batch ESSR is defined as:

$$ESSR \text{ (batch)} = \frac{\text{volumetric flow rate of stripping fluid (at STP)} \times \text{stripping time}}{\text{volume of catalyst}}$$

Note that both the ESSR and ESSR (batch) characterize the amount of stripping fluid used to strip a given amount of catalyst.

In the one particular embodiment a combination of stripping times between approximately 0.2 and 30 minutes at a volumetric flow rate of about 18 mL/min and a catalyst volume of 0.012 mL. Using the formula given above, these conditions correspond to an ESSR (batch) of 300 to 4500 respectively. These are far above the ESSRs typically used in conventional integrated catalytic-regeneration processes such as Fluid Catalytic Cracking (FCC). In a typical stripping process in FCC ESSRs in the range of 1.25 and 5 are used. In the current invention, a stripper employing an ESSR between approximately 10 and 10,000 is preferred, more preferred is a stripper employing an ESSR between approximately 20 and 5000 and most preferred are strippers employing ESSRs between approximately 30 and 4500.

With reference to FIG. 3, stripped catalyst can then be directed to the inlet of the reaction zone 1 to repeat the cycle or optionally, directed to a regenerator 4 or, more preferably, split into two streams, one directed to the reaction zone 1 and a second directed to a regenerator 4.

Despite the reduced rate in which coke deposits on the catalyst due to the process of the invention, the coke that does form will need to be removed via regeneration. Coked catalyst can be regenerated, after the stripping step, by contacting at least a portion of the coked catalyst with a regeneration medium to remove all or part of the coke deposits. This regeneration can occur periodically within the reactor by ceasing the flow of feed to the reactor, introducing a regeneration medium, ceasing flow of the regeneration medium, and then reintroducing the feed to the fully or partially regenerated catalyst. Preferably regeneration will occur periodically or continuously outside the reactor by removing a portion of the deactivated catalyst to a separate regenerator, regenerating the coked catalyst in the regenerator, and subsequently reintroducing the regenerated catalyst to the reactor. Regeneration can occur at times and conditions appropriate to maintain a desired level of coke on the entire catalyst within the reactor.

As mentioned above, in the preferred embodiment of the continuous operation, only a portion of the catalyst is removed from the stripper and sent to the regenerator to remove the accumulated coke deposits that result during the catalytic reaction. In the regenerator, the catalyst is contacted with a regeneration medium containing oxygen or other oxidants. Examples of other oxidants include $O_3$, $SO_3$, $N_2O$, NO, $N_2O$, $N_2O_5$, and mixtures thereof. It is preferred to supply $O_2$ in the form of air. The air can be diluted with nitrogen, $CO_2$, flue gas, or steam. Generally, the $O_2$ concentration in the regenerator is maintained at a specific level to minimize overheating or the creation of hot spots in the spent or deactivated catalyst. The deactivated catalyst also may be regenerated reductively with $H_2$, CO, mixtures thereof, or other suitable reducing agents.

In essence, the coke deposits are removed from the catalyst during the regeneration process, forming a regenerated catalyst. The regenerated catalyst is then returned to the reactor for further contact with feed. Typical regeneration temperatures are in the range of 250–700° C., desirably in the range of 350–700° C. Preferably, regeneration is carried out at a temperature range of 450–700° C.

It may be desirable to cool at least a portion of the regenerated catalyst to a lower temperature before it is sent back to the reactor. A heat exchanger located externally to the regenerator may be used to remove some heat from the catalyst after it has been withdrawn from the regenerator. When the regenerated catalyst is cooled, it is desirable to cool it to a temperature which is from about 200° C. higher to about 200° C. lower than the temperature of the catalyst withdrawn from the reactor. More desirably, it is cooled to a temperature from about 10–200° C. lower than the temperature of the catalyst withdrawn from the reactor. This cooled catalyst then may be returned to either some portion of the reactor, the regenerator, or both. When the regenerated catalyst from the regenerator is returned to the reactor, it may be returned to the reactor's catalyst disengaging zone, the reaction zone, and/or the inlet zone. Introducing the cooled catalyst into the reactor or regenerator serves to reduce the average temperature in the reactor or regenerator.

In one embodiment, the reactor and regenerator are configured such that the feed contacts the regenerated catalyst before it is returned to the reactor. In an alternative embodiment, the reactor and regenerator are configured such that the feed contacts the regenerated catalyst after it is returned to the reactor. In yet another embodiment, the feed stream can be split such that feed contacts regenerated catalyst before it is returned to the reactor and after it has been returned to the reactor.

It is preferred that the catalyst within the reactor have an average level of coke effective for selectivity to ethylene and/or propylene. Preferably, the average coke level on the catalyst will be from about 2 wt. % to about 30 wt. %, more preferably from about 2 wt. % to about 20 wt. %. In order to maintain this average level of coke on catalyst, the entire volume of catalyst can be partially regenerated under conditions effective to maintain the desired coke content on catalyst. It is preferred, however, to recycle only a portion of the coked catalyst for feed contact without regenerating. This recycle can be performed either internal or external to the reactor. The portion of coked catalyst to be regenerated is preferably regenerated under conditions effective to obtain a regenerated catalyst having a coke content of less than 2 wt. %, preferably less than 1.5 wt. %, and most preferably less than 1.0 wt. %.

In order to make up for any catalyst loss during the regeneration or reaction process, fresh catalyst can be added. Preferably, the fresh catalyst is added to the regenerated catalyst after it is removed from the regenerator, and then both are added to the reactor. However, the fresh catalyst can be added to the reactor independently of the regenerated catalyst. Any amount of fresh catalyst can be added, but it is preferred that an ACFE index of at least 1.5 be maintained.

One skilled in the art will also appreciate that the olefins produced by the oxygenate-to-olefin conversion reaction of the present invention can be polymerized to form polyolefins, particularly polyethylene and polypropylene. Processes for forming polyolefins from olefins are known in the art. Catalytic processes are preferred. Particularly preferred are metallocene, Ziegler/Natta and acid catalytic systems. See, for example, U.S. Pat. Nos. 3,258,455; 3,305, 538; 3,364,190; 5,892,079; 4,659,685; 4,076,698; 3,645, 992; 4,302,565; and 4,243,691, the catalyst and process descriptions of each being expressly incorporated herein by reference. In general, these methods involve contacting the olefin product with a polyolefin-forming catalyst at a pressure and temperature effective to form the polyolefin product.

A preferred polyolefin-forming catalyst is a metallocene catalyst. The preferred temperature range of operation is between 50 and 240° C. and the reaction can be carried out at low, medium or high pressure, being anywhere within the range of about 1 to 200 bars. For processes carried out in solution, an inert diluent can be used, and the preferred operating pressure range is between 10 and 150 bars, with a preferred temperature range of between 120 and 230° C. For gas phase processes, it is preferred that the temperature generally be within a range of 60 to 160° C., and that the operating pressure be between 5 and 50 bars.

In addition to polyolefins, numerous other olefin derivatives may be formed from the olefins recovered therefrom. These include, but are not limited to, aldehydes, alcohols, acetic acid, linear alpha olefins, vinyl acetate, ethylene dicholoride and vinyl chloride, ethylbenzene, ethylene oxide, cumene, isopropyl alcohol, acrolein, allyl chloride, propylene oxide, acrylic acid, ethylene-propylene rubbers, and acrylonitrile, and trimers and dimers of ethylene, propylene or butylenes. The methods of manufacturing these derivatives are well known in the art, and therefore, are not discussed herein.

This invention will be better understood with reference to the following examples, which are intended to illustrate specific embodiments within the overall scope of the invention as claimed. Examples 1–4 compare the catalyst activity of the catalyst that is used in a reaction process in accordance with the invention with a catalyst that is used in a conventional, continuous flow reactor.

EXAMPLE 1

A sample of SAPO-34 prepared from morpholine template was tested for performance in a pulse type reactor as shown by run "A" in FIG. 1. Chemical analysis of this catalyst revealed an atomic Si/Al ratio of about 0.678. Thus, the catalyst used in Example 1 and 2 have a relatively high level of acidity.

Calcined catalyst, 12.5 mg, was transferred to a 4 mm diameter quartz reactor. The reactor was inserted into a heated block at about 450° C. with a total pressure of about 25 psig and a calculated WHSV of approximately 140 hr$^{-1}$. Inert carrier gas continuously flowed through the reactor and simulated stripping of the catalyst. Methanol was repetitively injected over the catalyst in 1 μl aliquots. For some injections, sufficient time (30 minutes) was provided to analyze the products before the next injection was made. In other cases, multiple injections of methanol were made with about 12 seconds between injections without analysis. A total of 9 g of methanol per gram of catalyst was processed.

The conversions were based on hydrocarbon appearance on a water free basis and excluded coke yields. The intermediate product dimethyl ether was treated as if it were unreacted feed.

EXAMPLE 2

A sample of the morpholine templated SAPO-34, described in Example 1, was tested for performance in a continuous flow reactor as shown by run "B" in FIG. 1. Uncalcined catalyst, 0.62 g, diluted with 5 g of silicon carbide, was transferred to a ¾ inch diameter stainless steel reactor. Calcination was achieved in situ at 450° C. Reaction conditions were the same as in Example 1, except that methanol was pumped through the catalyst bed at a rate of 0.165 ml/min, which led to a WHSV of 25 hr$^{-1}$. Feed was continued for a total of 28 minutes. Thus, a total of approximately 9 g of methanol per gram of catalyst was processed.

FIG. 1 compares the rates of methanol conversion for a pulse-type reactor, run A and a continuous reactor, run B, described in Examples 1 and 2, respectively. (first order rate constant $(-\ln(1-X)*WHSV)hr^{-1}$, where X is the conversion of methanol versus gMeOH per g catalyst). As shown, the catalyst activity (methanol conversion) is maintained at much greater values and for a much longer period of time for the purge type reactors conditions in comparison to the continuous flow conditions.

In order to simulate the stripping action of this invention, different types of reactors systems were used for run A and run B shown in FIG. 1. Consequently, it was necessary to use different amounts of catalyst and different flow rates. These differences were accounted for by normalizing the amount of feed oxygenate processed by the amount of catalyst used. As a result, the observed rates for each value of gram methanol fed per gram of catalyst provides a valid basis for comparing these results on a common basis.

EXAMPLE 3

A sample of dual-templated (TEAOH and DPA) SAPO-34 was tested for performance in a pulse type reactor in a similar manner as described above for Example 1. Chemical analysis of this catalyst revealed an atomic Si/Al$_2$ ratio of about 0.23. Thus, the catalyst used in Example 3 had a relatively low level of acidity.

The same procedure used as in Example 1 was repeated, except that a 12.7 mg sample of calcined catalyst was used.

EXAMPLE 4

A sample of the dual templated SAPO-34, described in Example 3, was tested for performance in a continuous flow reactor. The same procedure used as in Example 2 was repeated.

Figure 2:
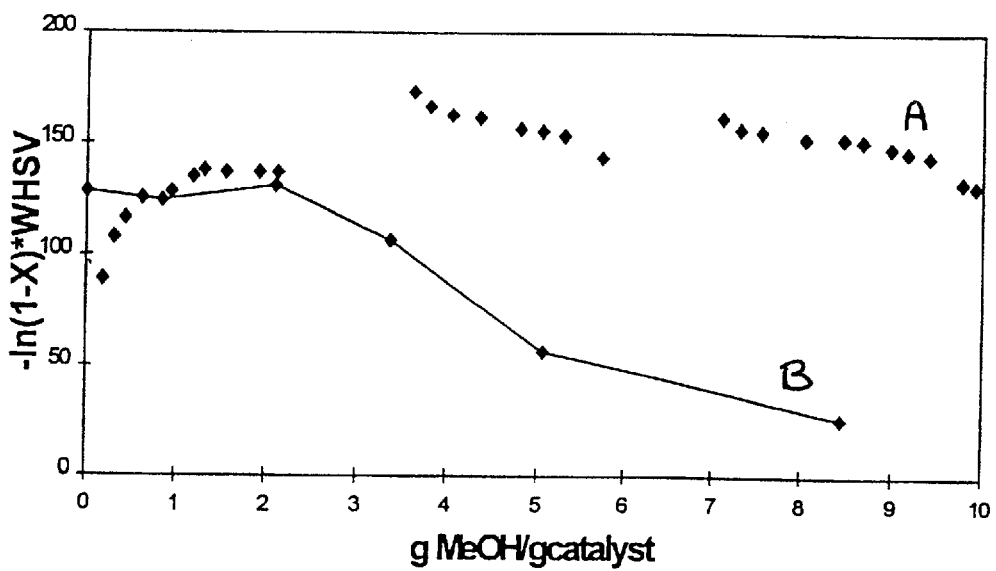
FIG. 2 illustrates the increase in catalytic activity using a TEAOH and DPA dual-templated SAPO-34 catalyst and the process of the present invention compared with conventional continuous flow reactor.

FIG. 2 compares the rates of methanol conversion for a pulse-type reactor, run A and a continuous reactor, run B, described in Examples 3 and 4, respectively. (first order rate constant $(-\ln(1-X)*WHSV)hr^{-1}$, where X is the conversion of methanol versus gMeOH per g catalyst). As in FIG. 1, the catalyst activity is maintained at greater values and for a longer period of time under pulse reaction conditions, run A, in comparison to the continuous flow conditions, run B. Further, in comparing FIG. 2 with FIG. 1, the disadvantage of a continuous flow reactor is shown to be less significant when a dual templated catalyst is used relative to the morpholine catalyst. As a result, the benefits of the present invention provide greater benefits for catalysts with relatively high Si/Al ratios (greater than 0.30) that is, catalysts having a relatively higher number of acid sites.

Having now fully described this invention, it will be appreciated by those skilled in the art that the invention can be performed within a wide range of parameters within what is claimed, without departing from the spirit and scope of the invention.

What is claimed is:

1. A method for the production of olefin product from an oxygenate-containing feedstock, comprising exposing a silicoaluminophosphate molecular sieve catalyst to the oxygenate-containing feedstock in a reaction zone under conditions effective to convert the oxygenate-containing feedstock to an olefin product, resulting in an exposed catalyst, wherein the silicoaluminophosphate molecular sieve has a Si/Al atomic ratio of at least 0.30;

stripping at least a portion of the exposed catalyst with a stripping gas, resulting in a stripped catalyst; and returning at least a portion of the stripped catalyst to the reaction zone without regenerating.

2. The method of claim 1, further comprising regenerating at least a portion of the stripped catalyst and returning at least a portion of the regenerated catalyst to the reaction zone.

3. The method of claim 1, wherein a ratio defined by time of exposing the catalyst to the oxygenate containing feedstock to time of stripping the exposed catalyst with the stripping gas is from 1:1 to 20:1.

4. The method of claim 1, wherein a ratio defined by time of exposing the catalyst to the oxygenate containing feedstock to time of stripping the exposed catalyst with the stripping gas is greater than 20:1.

5. The method of claim 1, wherein the stripping gas is selected from the group consisting of steam, nitrogen, air, helium, argon, methane, carbon dioxide, carbon monoxide, flue gas, hydrogen, and combinations thereof.

6. The method of claim 1 wherein the stripping gas comprises steam.

7. The method of claim 6 wherein the stripping gas flows at a rate of 1 to 10 lbs per hour per 1000 lbs of catalyst per hour.

8. The method of claim 7 wherein the stripping gas flows at a rate of 1 to 4 lbs per hour per 1000 lbs of catalyst per hour.

9. The method of claim 1, wherein the stripped catalyst is stripped in a separate unit apart from the regenerator.

10. The method of claim 1, wherein the stripping of the exposed catalyst removes at least 25% of the hydrocarbons adhered thereto.

11. The method of claim 1, wherein the stripping of the exposed catalyst removes at least 50% of the hydrocarbons adhered thereto.

12. The method of claim 1 wherein the stripped catalyst contains less than 10% by weight of hydrocarbons selected from the group consisting of olefins, aromatics, parafins, oxygenates, and mixtures thereof.

13. The method of claim 1, wherein the oxygenate-containing feedstock comprises at least one compound selected from the group consisting of methanol; ethanol; n-propanol; isopropanol; $C_4$–$C_{20}$ alcohols; methyl ethyl ether; dimethyl ether; diethyl ether; di-isopropyl ether; formaldehyde; dimethyl carbonate; dimethyl ketone; acetic acid; and mixtures thereof.

14. The method of claim 1, wherein the silicoaluminophosphate molecular sieve catalyst comprises a silicoalumninophosphate molecular sieve and a binder.

15. The method of claim 14, wherein the silicoaluminophosphate molecular sieve is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, metal containing forms thereof, and mixtures thereof.

16. The method of claim 1, wherein the reaction zone comprises temperatures of about 350 to 550° C. while exposing the molecular sieve catalyst to the oxygenate-containing feedstock.

17. The method of claim 1, wherein the oxygenate-containing feedstock contacts the molecular sieve catalyst in the reaction zone at an average gas superficial velocity of greater than 1 meter per second.

18. The method of claim 1, further comprising contacting the olefin product with a polyolefin-forming catalyst under conditions effective to form a polyolefin.

19. The method of claim 1, wherein the stripping at least a portion of the exposed catalyst with a stripping gas is carried out intermittently, thereby controlling the manner in which coke is deposited on the catalyst.

* * * * *